US010524812B2

(12) United States Patent
Peyrard et al.

(10) Patent No.: US 10,524,812 B2
(45) Date of Patent: Jan. 7, 2020

(54) METHOD AND APPARATUS FOR LOCATING AND VISUALIZING A TARGET IN RELATION TO A FOCAL POINT OF A TREATMENT SYSTEM

(75) Inventors: Andre Peyrard, Saint Christophe en Jarez (FR); Claire Vurpillot, Villeurbanne (FR); Rene Chatre, Venissieux (FR)

(73) Assignee: EDAP TMS FRANCE, Vaulx-En-Velin (FR)

( * ) Notice: Subject to any disclaimer, the term of this patent is extended or adjusted under 35 U.S.C. 154(b) by 321 days.

(21) Appl. No.: 12/977,864

(22) Filed: Dec. 23, 2010

(65) Prior Publication Data

US 2011/0166450 A1 Jul. 7, 2011

(30) Foreign Application Priority Data

Jan. 5, 2010 (FR) ...................................... 10 50041

(51) Int. Cl.
*A61B 17/225* (2006.01)
(52) U.S. Cl.
CPC ................................ *A61B 17/2255* (2013.01)
(58) Field of Classification Search
USPC ........................................................ 600/439
See application file for complete search history.

(56) References Cited

U.S. PATENT DOCUMENTS

| 4,896,673 A | 1/1990 | Rose et al. |
| 5,295,483 A | 3/1994 | Nowacki et al. |
| 5,315,986 A | 5/1994 | Lacruche et al. |
| 5,944,663 A | 8/1999 | Kuth |

(Continued)

FOREIGN PATENT DOCUMENTS

| DE | 195 12 956 A1 | 10/1996 |
| DE | 198 41 951 A1 | 4/2000 |

(Continued)

OTHER PUBLICATIONS

Espacenet English abstract of DE 198 41 951 A1.
Espacenet English abstract of DE 195 12 956 A1.
Espacenet English abstract of JP 2000-237205 A.
J-PlatPat English translation of JP 2000-237205 A.
Wintermantel, et al., Medizintechnik—Life Science Engineering (1995), pp. 2449-2468, Springer, Germany. (partial English translation).

(Continued)

*Primary Examiner* — Thomas J Hong
*Assistant Examiner* — Shahdeep Mohammed
(74) *Attorney, Agent, or Firm* — Ladas & Parry LLP; Malcolm J. MacDonald

(57) ABSTRACT

A method for locating and visualizing a target (C) in relation to a focal point (F2), in a mammal, particularly a human body, including the steps of forming an ultrasound probe mobile in space, mechanically independent of a treatment system and located by a remote locating system, ensuring simultaneous recording firstly of an ultrasound image in which the image of the target appears, and secondly of the position of the ultrasound probe, in the recorded ultrasound image, selecting the position of the image of the target to determine the virtual position of the target (C), simultaneously determining firstly the position of the focal point (F2) by the remote locating system, and secondly the position of the members displacing the target and/or treatment system, and calculating the displacement values for the displacing members, to cause the virtual position of the target (C) to coincide with the focal point (F2).

14 Claims, 3 Drawing Sheets

(56) References Cited

U.S. PATENT DOCUMENTS

| | | | |
|---|---|---|---|
| 6,006,126 A * | 12/1999 | Cosman | G06K 9/3216 600/414 |
| 6,122,541 A * | 9/2000 | Cosman | A61B 90/10 600/426 |
| 6,126,600 A * | 10/2000 | Oxaal | G01S 15/8906 600/439 |
| 6,860,853 B2 * | 3/2005 | Hashimoto | 600/446 |
| 7,510,536 B2 * | 3/2009 | Foley et al. | 600/439 |
| 7,610,079 B2 | 10/2009 | Schwarze et al. | |
| 2001/0039379 A1 | 11/2001 | Hagelauer | |
| 2003/0149352 A1 | 8/2003 | Liang et al. | |
| 2003/0204139 A1 | 10/2003 | Hashimoto | |
| 2004/0106861 A1 * | 6/2004 | Leitner | 600/407 |
| 2005/0240126 A1 | 10/2005 | Foley et al. | |
| 2006/0025677 A1 * | 2/2006 | Verard et al. | 600/423 |
| 2008/0015436 A1 * | 1/2008 | Mikus | A61B 8/0833 600/439 |
| 2008/0177279 A1 * | 7/2008 | Sumanaweera et al. | 606/130 |
| 2008/0306378 A1 * | 12/2008 | Trousset et al. | 600/424 |
| 2009/0216122 A1 * | 8/2009 | Faragalla | A61B 8/4416 600/439 |

FOREIGN PATENT DOCUMENTS

| | | |
|---|---|---|
| DE | 10 2004 006 021 | 9/2005 |
| DE | 10 2006 060 070 | 2/2008 |
| JP | 2000-237205 A | 9/2000 |

OTHER PUBLICATIONS

Digital photographs taken at the 22nd Annual Congress of European Association of Urology AST GmbH booth, held in Berlin, Germany, on Mar. 21, 2007 to Mar. 24, 2007. Attestation by Dr. Werner Schwarze.

LithoSpace® Operator Manual (2009). (partial English translation).

An Overview of EAU Congress History: 22nd Annual EAU Congress, Mar. 21-24, 2007, Berlin, Germany.

AST The Shockwave Experts: (circa. May 2007).

Record of Delivery, Advanced Shockwave Technology GmbH, 2009.

Course of Instruction, Advanced Shockwave Technology GmbH, Mar. 5, 2010.

* cited by examiner

METHOD AND APPARATUS FOR LOCATING AND VISUALIZING A TARGET IN RELATION TO A FOCAL POINT OF A TREATMENT SYSTEM

BACKGROUND OF THE INVENTION

The subject matter of the invention relates to the technical field of visualizing and locating an anatomic structure or concrement in the body of a mammal, a human being in particular.

The locating and visualization of anatomic structures or concrements generally designated as targets in the remainder of the description, are currently performed using imaging devices based on different methods such as echography methods using ultrasound, or tomography methods based on X-rays, or on magnetic resonance (MRI). These imaging devices therefore allow the positioning of a therapeutic treatment system in relation to the target for treatment thereof by focusing shock waves or ultrasound waves on a focal point.

In the state of the art, a treatment apparatus is known from document DE 10 2006 060070, which comprises a system for treatment with acoustic pressure waves, using an imaging system of X-ray type, even if said document provides for the possible use of an imaging system of acoustic type. Said X-ray imaging system is mounted on a carrier structure that is mobile relative to the frame of the apparatus. Said apparatus also comprises a remote locating system allowing detection of the position of the treatment system and imaging system. The apparatus comprises a display screen on which the focal point of the treatment system and the target to be treated are visualized. The treatment system is moved to cause the focal point and the target to be treated to coincide.

Along the same lines, document DE 10 2004 006021 similarly describes a treatment apparatus in which there is no mechanical link between the imaging system, the therapy system and the table supporting the patient. This document describes a technique which, by means of the X-ray imaging system, is used to align the focal point of the therapy system with the target to be treated. The document teaches taking a series of X-ray pictures from two angles and identifying in each of the pictures the iso-centre of the imaging system, the focal point of the therapy system and the target, then of causing the focal point and the target to coincide by moving either one thereof, bearing in mind that all the degrees of freedom associated with these movements are provided with encoders allowing determination of values of movement.

It is to be noted that the physical principle of image projection by an imaging system of X-ray type allows visual tracking of the alignment of the target and focal point, since this imaging system is permanently oriented to monitor the volume located around the focal point. However, in general, imaging systems of X-ray type are costly, complex and cumbersome which means that it appears difficult to use these in combination with treatment systems. Also, the monitoring of the alignment of the target and focal point using X-rays requires continuous irradiation of the patient, which is harmful for the patient and nursing staff.

Ultrasound systems, on the other hand, are more compact, less costly and can easily be used in combination with therapeutic treatment systems. In addition, contrary to X-ray devices, ultrasound systems do not emit any ionizing radiation.

In the state of the art, there are numerous embodiments of apparatus which combine an ultrasound probe of an imaging system with a treatment system focusing waves on a focal point. In general, the locating device allows the target to be treated and the focal point of the treatment apparatus to be visualized in the image. Causing the target to coincide with the focal point is obtained by moving either the focal point of the treatment system, or the target i.e. the table supporting the patient. This coinciding evidently requires knowledge of the orientation of the image plane in relation to the axes of mechanical movement of the table or treatment apparatus. By measuring the coordinates of the target and focal point in the image, and from knowledge of the orientation of the image plane, it is possible to calculate the distance separating the target and the focal point and to move the focal point, namely the treatment device or the target, to cause them to coincide.

In the state of the art, it is known, notably from EP 0 404 871 or U.S. Pat. No. 5,078,124, to position the ultrasound probe of the imaging system so that it permanently targets the focal point of the treatment apparatus and so that this focal point continually appears in the image. The axis of the image plane passes through the focal point of the therapy apparatus. To cause the target to appear on the same image plane, the operator can either move the patient so that the image of the target appears in the ultrasound image, or move the ultrasound probe about its axis targeting the focal point until the target appears in the ultrasound image.

It is to be considered that the ultrasound probe is always joined to a mechanical holder targeting the focal point of the treatment apparatus. This constraint is extremely penalising for the operator, insofar as it appears difficult in some cases to find the target having regard to the limited movements of the probe and/or patient to obtain the target and focal point in one same image. Also, it appears difficult to adjust the plane of the ultrasound image slice relative to the anatomy of the observed target to obtain the best possible definition of the contours or inner side of the target.

It is to be noted that U.S. Pat. No. 5,944,663 describes a treatment method comprising a focused ultrasound source which is not combined with an imaging device. Imaging of the patient is performed during a phase prior to the treatment phase. This method provides for causing the marking of the imaging device to coincide with the marking of the therapy device. This coinciding is achieved through the presence of markers positioned on the table supporting the patient, and which are visualized by the locating system during each of the imaging then therapy phases. The images of the patient are positioned in relation to the table markers which are identified in marking associated with the imaging device. These same markers are then positioned in the marking associated with the therapy device. The therapy probe is positioned within this same marking by means of a second set of markers joined to the therapy device. Therefore, with said method it is possible, within one same reference marking, to arrange the entire dataset required to cause patient imaging to coincide with the treatment region, in order to display the position of the focal point in the image volume.

The main drawback with this technique concerns the fact that imaging is not carried out in real time, since imaging is conducted during a phase prior to the treatment phase. This technique does not allow monitoring and confirmation of the correct positioning of the therapy device in relation to the targeted region. This approach is based on full immobility of the patient during the treatment phase, which appears difficult to implement in practice.

SUMMARY OF THE INVENTION

The present invention therefore sets out to remedy the disadvantages set forth above by proposing a novel technique which offers the advantage of facilitating the locating operation of an anatomic target by means of an ultrasound imaging system, whilst allowing the precise positioning of a treatment system using acoustic pressure waves to treat said target.

To attain this objective, the subject matter of the invention concerns a method to locate and visualize a target belonging to a mammal, a human being in particular, in relation to a focal point of a treatment system which uses acoustic pressure waves, by means of an ultrasound imaging system comprising an ultrasound probe and at least one image display screen, the target and/or the treatment system being moved by displacing means to cause the target and focal point to coincide.

According to the invention the method comprises the following steps:

forming an ultrasound probe mobile in space, mechanically independent of the treatment system and located by a remote locating system when it lies within its detection volume, moving the ultrasound probe within the detection volume to visualize the target in an image displayed in the screen, simultaneously recording firstly an ultrasound image in which the image of the target appears, and secondly the position of the ultrasound probe, selecting the position of the image of the target in the recorded ultrasound image, to determine the virtual position of the target, simultaneously determining firstly the position of the focal point of the treatment system by means of the remote locating system, and secondly the position of the displacing means used to move the target and/or treatment system, from the virtual position of the target and the positions of the focal point and displacing means, calculating the displacement values for the displacing means to allow coinciding of the virtual position of the target with the focal point, and moving the target and/or focal point by means of the displacing means and in accordance with calculated displacement values, so as to cause the virtual position of the target to coincide with the focal point.

The method of the invention also comprises in combination any one and/or other of the following characteristics:

determining the position of the displacing means by means of the remote positioning system, ensuring the display of the calculated displacement values for the displacing means, and updating these displayed displacement values in relation to the displacement made, visualizing on the screen the virtual image of the target with the image of the focal point, and movement thereof when causing the virtual image of the target to coincide with the focal point via the displacing means, ensuring the display of two virtual images taken in two secant planes and causing to appear in each thereof the virtual image of the position of the target and the virtual image of the position of the focal point, and their relative movements subsequent to movement by the displacing means, by means of the remote positioning system, visualizing the orientation of the focal volume of the treatment system, a step to confirm the coinciding of the focal point with the target, consisting of:

moving the ultrasound probe to locate the target, to allow display of the image of the target on the screen, ensuring the recording of the position of the focal point and display of the image of the focal point to verify the coinciding of the focal point with the target, with a view to operating the treatment system, the confirmation step, in the event of offset between the focal point and the target, consists of:

moving the ultrasound probe to visualize the target in an image displayed on the screen, simultaneously recording firstly the image in which the image of the target appears, and secondly the position of the ultrasound probe, selecting the position of the image of the target in the recorded image, simultaneously determining the position of the focal point and the position of the displacing means, calculating displacement values for the displacing means, to allow coinciding of the focal point with the virtual position of the target, and moving the target and/or focal point via the displacing means so as to cause the virtual position of the target to coincide with the focal point, displaying the image of the focal point in a position independent of the sighting axis of the ultrasound probe.

A further subject matter of the invention concerns an apparatus to locate and visualize a target belonging to a mammal, a human being in particular, this apparatus comprising:

a treatment system using acoustic pressure waves directed towards a focal point, displacing means to move the target and/or treatment system so as to cause the target to coincide with the focal point, means to determine the position of these displacing means, an ultrasound imaging system comprising an ultrasound probe and image forming means allowing the target and focal point to be visualized at least on one screen.

According to the invention, the apparatus comprises:

an ultrasound probe mobile in space and mechanically independent of the treatment system, a system for the remote locating of objects allowing the locating of the focal point of the treatment system and the ultrasound probe when the ultrasound probe and the treatment system lie in the detection volume of said locating system, a computing and control unit comprising:

means for simultaneously recording firstly an ultrasound image in which the image of the target appears, and secondly the position of the ultrasound probe detected and computed by the remote locating system, means for selecting the position of the image of the target in the recorded ultrasound image, to determine the virtual position of the target, means for simultaneously determining firstly the position of the focal point by means of the remote locating system, and secondly the position of the displacing means, means for computing displacement values for the displacing means, from the virtual position of the target and the positions of the focal point and displacing means, to cause the virtual position of the target to coincide with the focal point, and means for controlling the displacing means, as per the calculated displacement values, to cause the virtual position of the target to coincide with the focal point.

The apparatus according to the invention also comprises in combination one and/or other of the following characteristics:

the means for determining the position of the displacing means are part of the remote locating system, the remote locating system comprises at least two, preferably infrared, cameras comprising a detection volume in which a first, a second and even a third marker are positioned joined to the ultrasound probe, treatment system and target displacing means respectively, the third marker joined to the displacing means is oriented along the displacement axes of said displacing means, the remote locating system comprises a calibration marker for the focal point, means ensuring the display of the displacement values calculated for the displacing means, these displayed values being updated in relation to the displacement made, means for visualizing on the screen the virtual image of the target, the image of the focal point and movement thereof by the displacing means when causing the virtual image of the target to coincide with the focal point, means for displaying two virtual images taken along two secant planes and causing to appear in each thereof the virtual image of the position of the target, the virtual image of the position of the focal point, and their respective movements subsequent to movement by the displacing means, the display means form an image displaying the image plane delivered by the ultrasound probe and the focal point.

BRIEF DESCRIPTION OF THE DRAWINGS

Various other characteristics will become apparent from the description given below with reference to the appended drawings which, as non-limiting examples, illustrate embodiments of the subject matter of the invention.

DESCRIPTION OF THE PREFERRED EMBODIMENTS

Figure 1:
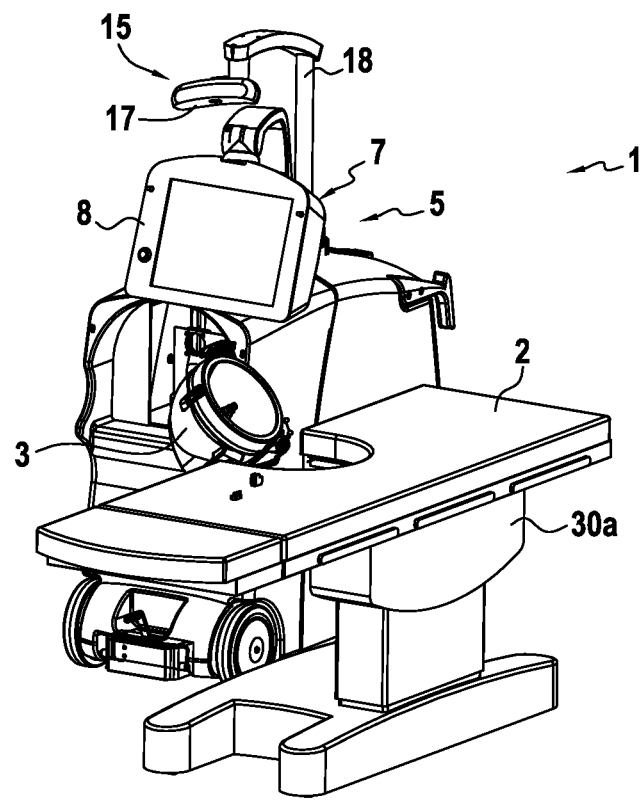
FIG. 1 is a perspective view illustrating an embodiment of a locating and visualizing apparatus according to the invention.
Figure 2:
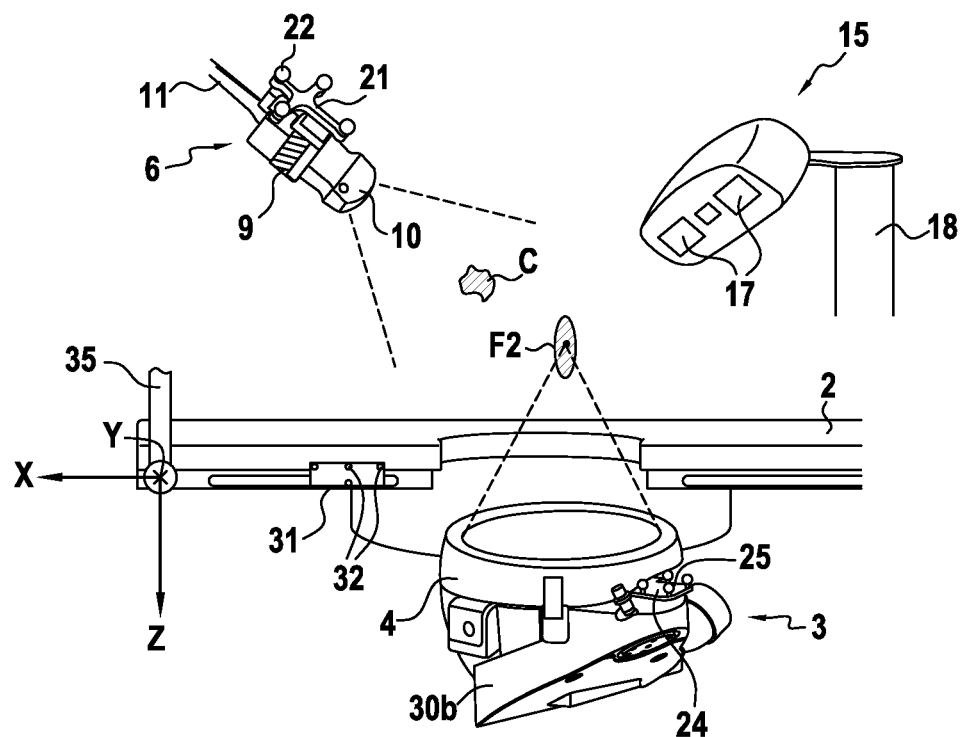
FIG. 2 is a schematic view illustrating characteristic details of the locating and visualizing apparatus according to the invention.

FIGS. 1 and 2 illustrate apparatus 1 for the locating and visualization of a target C such as an anatomic structure or concrement belonging to a mammal, a human being in particular. As is conventional, the apparatus 1 comprises a table 2 supporting a patient carrying the target C. The target C is intended to be treated by means of a treatment system 3 using acoustic pressure waves directed towards a focal point F2. Said treatment system 3 ensures the focusing of shock waves or ultrasound waves. As is conventional, this treatment system 3 comprises a generator 4 designed to focus the ultrasound waves or shock waves on a focal point F2. The treatment system 3 is not described in further detail since it is well known to the person skilled in the art and is not specifically part of the subject matter of the invention.

The apparatus 1 conforming to the invention also comprises an ultrasound imaging system 5 comprising an ultrasound probe 6 connected to image forming means 7 on a screen 8. Said ultrasound imaging system 5 allows the display on the screen 8 of at least one ultrasound image obtained by the probe 6. According to one preferred variant of embodiment, the screen 8 is of touch-screen type. This ultrasound imaging system 5 is not described more precisely, since said system is well known to the person skilled in the art of ultrasound or echography and will not be described in further detail.

The ultrasound imaging system 5 is connected to a computing and control unit forming part of the apparatus 1 conforming to the invention. This computing and control unit comprises different means, notably recording, computing, display, control means adapted to perform various functions which will become more precisely apparent in the remainder of the description. Also, the apparatus 1 is connected to the treatment system 3 to guide the functioning thereof.

According to one characteristic of the invention, the ultrasound probe 6 is mechanically independent of the treatment system 3. As can be seen more precisely in FIG. 2, this ultrasound probe 6 comprises a main body 9 provided at its distal part with an ultrasound transducer 10. This ultrasound probe 6 is covered by a shell forming a grasping handle. The ultrasound probe 6 is equipped at its proximal part with an electric connection cable 11 to the image forming means 7. This ultrasound probe 6 is therefore solely linked via the electric connection cable 11 to the image forming means 7. The ultrasound probe 6 is therefore not mechanically linked to the treatment system 3. The ultrasound probe is therefore mechanically free in relation to the treatment system 3.

It is to be understood that the ultrasound probe 6 is free to move in space, thereby offering the operator large freedom of movement when displacing the ultrasound probe, enabling permanent adjustment of the image slice plane with respect to the patient's anatomy to obtain the best possible definition of an or organ or of the target C inside an organ.

The apparatus 1 according to the invention also comprises a remote object locating system 15 in particular allowing the focal point F2 of the treatment system 3 and the ultrasound probe 6 to be located when the ultrasound probe 6 and the focal point F2 lie within a detection volume of the locating system 15. The remote locating system 15 can have recourse to all types of detection techniques. Advantageously, the locating system 15 is a detection system of infrared electromagnetic radiation type.

According to the advantageous variant of embodiment, the locating system 15 comprises at least two infrared detection cameras 17 mounted on a support 18. The cameras 17 are oriented so as to define a detection volume in which a first marker is positioned 21 attached to the ultrasound probe 6. Preferably, the first marker 21 is attached onto the body 9 of the ultrasound probe 6 so as not to hamper grasping of the ultrasound probe. Similarly, grasping of the ultrasound probe 6 must not mask the first marker 21 with respect to the locating system 15.

The first marker 21 comprises at least three, and in the illustrated example four reflective spheres 22 whose positions relative to one another are known. The fourth reflective sphere 22 is redundant with the three others to improve the precision of spatial locating. This first marker 21 can be visualized simultaneously by the two cameras 17 allowing observation thereof from two different angles. The locating system 15 therefore has two images each containing reflective spheres of the first marker 21. Analysis of these images allows the extraction of six positional data items which are needed to calculate the six degrees of freedom regarding the position and orientation of the ultrasound probe 6, namely three degrees of freedom for position and three degrees for orientation.

With said locating system 15, it is possible to determine the position of the ultrasound probe 6 in space, and in particular in the detection volume of the infrared cameras 17. The position and orientation of the ultrasound probe 6 are calculated within a reference system associated with the cameras 17 for example. The position of the ultrasound probe 6 can therefore be represented by a vector with which a position and a direction are associated.

According to another characteristic of the invention, the system 15 for the remote locating of objects also allows the locating of the focal point F2 of the treatment system 3, when the focal point lies within the detection volume of the cameras 17. The treatment system is therefore equipped with a second marker 24 comprising at least three, and in the illustrated example four reflective spheres 25 whose positions relative to one another are known. This second marker 24 is also visualized simultaneously by the two cameras 17 allowing observation thereof from two different angles. The locating system 15 is capable of calculating the spatial position of the treatment system 3 within the same marking as the one associated with the first marker 21 attached to the ultrasound probe 6.

In the illustrated example, the second marker 24 is attached to the body of the generator 4 and therefore indirectly represents the position of the focal point F2. It appears necessary to determine the transfer matrix giving the position of the focal point F2 relative to the second marker 24. The determination of this transfer matrix is performed during a calibration phase implemented at the time of manufacture or installation of the apparatus 1. This calibration phase consists of pointing the focal point F2 with a calibration tool not illustrated but equipped with another marker of the type of the first and second markers 21, 24 and of calculating the transfer matrix between this marker and the second marker 24.

It is to be noted that only the position of the focal point F2 in the detection volume is necessary to cause the focal point F2 to coincide with the target C. According to one advantageous embodiment, the locating 15 provides access to the spatial orientation of the second marker 24. This information on spatial orientation can then be used to represent or visualize the direction of the acoustic cone and the orientation of the focal volume or propagation of acoustic waves and display thereof on a screen, e.g. screen 8.

The locating system 15 provides the apparatus 1 with information on the location of the ultrasound probe 6 and focal point F2. The apparatus 1 comprises means to record the position of the ultrasound probe 6 and the position of the focal point F2. The apparatus 1 also comprises means to ensure the display, on screen 8, of the image of the position of the target C and the image of the position of the focal point F2 as will be described in the remainder of the description.

The apparatus 1 according to the invention also comprises displacing means to move the target C and/or treatment system 3 so that the target C and focal point F2 coincide. The displacing means are of manual or motorized type. With respect to the supporting table 2, the displacing members 30a ensure movement of the table in three perpendicular directions X, Y, Z respectively corresponding to movement in the longitudinal direction, transverse and vertical directions of the table. In the remainder of the description, it is considered that the displacing means 2-30a allow movement of the target C, but the invention identically applies to displacing means 30b to move the treatment system 3.

The apparatus 1 according to the invention also comprises means allowing determination of the position of the displacing means 2-30a; 30b moving the target C and/or focal point F2. It is to be noted that the position of the focal point F2 is detected by the locating system 15 so that movement thereof is monitored by the second marker 24. The movement of the target C is ensured by movement of the table 2 supporting the patient which means that movement of the target C can be tracked by detection of the movement of the table 2.

One first solution is to equip the table 2 with sensors or movement encoders with a view to determining the position of the target C using a transfer matrix in the reference system of the focal point F2. To determine this transfer matrix, it is necessary to know the orientation of the axes of movement of the table 2 in the reference frame of the remote locating system 15. The table 2 and the remote locating system 15 and notably its cameras 17 must then occupy invariable relative positions when the transfer matrix is determined. In this case, recourse must be had to a rigid support 18 and checks and possible recalibrations must be regularly performed.

To avoid these checks, the subject matter of the invention according to one advantageous characteristic of embodiment, makes provision so that the means to determine the position of the displacing means 2-30a; 30b are part of the remote locating system 15. According to this advantageous variant of embodiment, the table 2 is equipped with a third marker 31 which is also visible by the two cameras 17. This third marker 31 comprises at least three, and in the illustrated example four reflective spheres 32 whose positions relative to one another are known. The locating system 15 therefore determines the spatial position of the table 2 within the same reference frame as the one associated with the first 21 and second 24 markers. The determination of the position of the table 2 and hence of the movement of the target t C allows tracking of the movement of the table 2 until the target C and the focal point F2 coincide.

Advantageously, this third marker 31 is oriented along three axes of movement of the table, namely axes OX, OY, OZ allowing calculation of the movement to be made within the reference frame X, Y, Z of the patient support, without having to calibrate the orientation of movements of the table 2 relative to the orientation of the third marker 31.

It is to be noted that this solution offers the advantage that the position of the cameras 17 may be any position and may vary from one locating procedure to another.

The locating system 15 transfers data to the apparatus 1 on the position of the displacing means 2-30a, 30b. The apparatus 1 is capable of recording the position of the displacing means and of displaying on the screen 8 the pathway taken by the displacing means, namely the pathway of the focal point F2 or the pathway of the target C, i.e. their position at each instant when being moved.

The apparatus 1 described above allows a novel and original method to be implemented for the locating and visualization of the target C.

Said method consists of installing the patient on the table 2 and of roughly positioning the patient with respect to the treatment system 3. After installation of the patient, the locating system 15 is activated and permanently detects the position of the first 21, second 24 and third 31 markers. The locating system 15 therefore permanently calculates the position of these three markers in the reference frame associated with the cameras 17 for example, so that data on the positions of the ultrasound probe 6, focal point F2 and table 2 are available at all times.

After taking hold of the ultrasound probe 6, the operator identifies the target C in the patient using the display of the ultrasound image on the screen 8. This identification phase is facilitated since the ultrasound probe 6 is mechanically independent of the treatment system 3. The operator therefore has available extensive freedom of movement to move the ultrasound probe 6, allowing permanent adjustment of the image slice plane in relation to the anatomy of the organ being observed. Evidently, the patient and the cameras 17 are positioned so that when the ultrasound probe 6 locates the target C, the ultrasound probe 6 lies within the detection volume of the locating system 15.

Figure 3A:
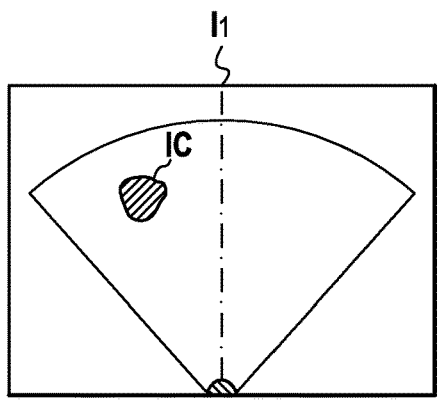
FIGS. 3A and 3B are schematic views illustrating an ultrasound image respectively showing the image of the target and the images of the target and focal point.

The ultrasound imaging system 5, throughout the entire identifying process of the target C, displays on the screen 8 the ultrasound image obtained by the ultrasound probe 6. As arises from FIG. 3A, the screen 8 therefore displays the ultrasound image $I_1$ which shows the image IC of the target C. The operator chooses the image $I_1$ in which the image IC of the target C appears the most distinct. This image $I_1$ is selected and recorded by the operator using any suitable means such as via a control member e.g. a pedal. Simultaneously with recording of the image $I_1$ chosen by the operator, the position of the ultrasound probe 6 detected and calculated by the locating system 15 is recorded. This recording is performed when activating the control member. The selected image $I_1$ is frozen i.e. it remains displayed on the screen 8.

The ultrasound probe 6 can then be freely put down without any positioning constraint in relation to the locating system 15.

Figure 3B:
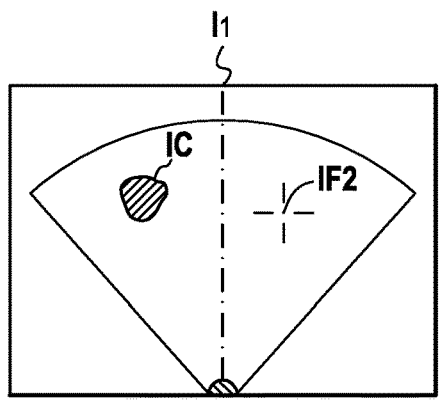

As follows more precisely from FIG. 3B, it is to be noted that the image IF2 of the focal point F2 can appear in the ultrasound image $I_1$ when the focal point lies in the plane of the ultrasound image. Therefore, according to one characteristic of the subject matter of the invention, the display of image IF2 of the focal point F2 is only made if the image plane lies secant to the focal point F2. The image IF2 of the focal point F2 therefore appears transiently on the screen 8, unlike the prior art in which the ultrasound image constantly displays the image of the focal point F2 since the plane of the ultrasound image always lies secant to the focal point F2 on account of the mechanical link between the ultrasound probe and the treatment device.

The following step of the method according to the invention consists of selecting the position of the image IC of target C in the recorded image $I_1$, so that the apparatus 1 is able to determine the position of the target C from the position of the ultrasound probe 6 simultaneously recorded with the recording of image $I_1$. Insofar as the position of the target C is determined from a recorded image, it is considered in the remainder of the description that this position corresponds to a virtual position of the target C. The selection of the position of the image IC of the target is advantageously made by pointing on the image IC of the target directly on the touch screen 8. Evidently, this selection can be made differently, for example using a mouse pointed on the image IC of the target.

Simultaneously with or after the selection of the position of the image IC of the target in the recorded image $I_1$, the position of the focal point F2 determined by the remote locating system 15 is recorded simultaneously with the recording of the position of the displacing means 2-30$a$, 30$b$ moving target C and/or the treatment system 3. In the example under consideration, the following are recorded simultaneously:

the position of the second marker 24 giving the position of the focal point F2, the position of the third marker 31 giving the position of the table 2 moving the target C.

The virtual position of the target C and the positions of the focal point F2 and table 2 are known within one same reference frame. The apparatus 1 performs calculations from the data on the virtual position of the target C and on the positions of the focal point F2 and table 2, to determine the displacement values for the displacing means to bring the target C and focal point F2 to coincide. According to one preferred variant of embodiment, only the table 2 is moved to cause the target C and focal point F2 to coincide.

The target C and/or the focal point F2 is moved to ensure this coinciding. In the illustrated example, it is the table 2 which is moved. If the table 2 is automatically motorized, the operator triggers the coinciding step so that the apparatus 1 guides the table 2 in accordance with the calculated displacement values to bring the target C to coincide with the focal point F2.

If coinciding is performed manually by the operator, assistance is provided by the display of the calculated displacement values. For example, provision can be made so that the displacement values of the table 2 are displayed on the screen 8, these values being continually updated in relation to the movement of the table 2. The operator then moves the table 2 until the calculated values become zero.

Advantageously, provision may be made, whether or not in combination with display of calculated displacement values, so that the apparatus 1 ensures display of the image of the focal point IF2, in relation to the virtual image of the target IC, so that the operator is able to move the target C (or focal point F2) using the displacing means, so as to cause the virtual image of the target IC to coincide with the image of the focal point IF2, aided by the display of the movement of the displacing means which is continually updated.

It is to be noted that it is not easy, in a three-dimensional image, to display the virtual image of the target C and the image of the focal point F2, so that this information is easily comprehensible by the operator.

Figure 3C:
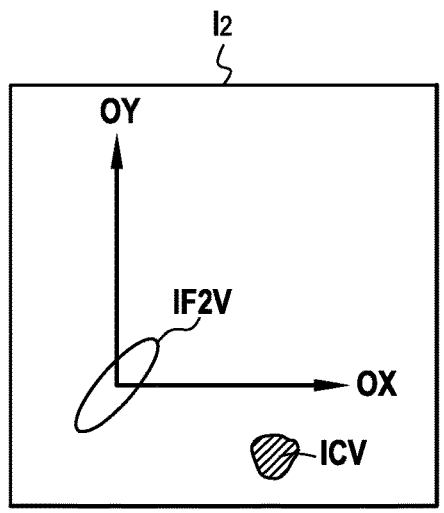
FIGS. 3C and 3D are schematic views of virtual images in each of which the image of the target and the image of the focal point can be seen.
Figure 3D:
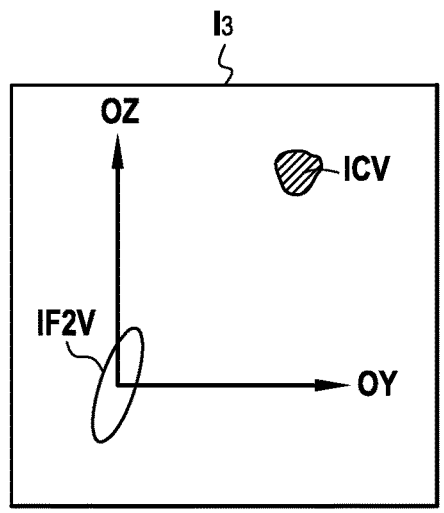

According to one preferred variant of embodiment, the display of the image of the focal point in relation to the virtual image of the target is achieved by creating at least two virtual images $I_2$, $I_3$ taken along two orthogonal secant planes and causing to appear in each thereof the virtual image of the position ICV of the target and the virtual image of the position IF2V of the focal point F2. As can be seen more precisely in FIGS. 3C and 3D, the screen 8 therefore displays two virtual images $I_2$, $I_3$ respectively taken along planes OY, OX and OZ, OY for example.

Figure 3E:
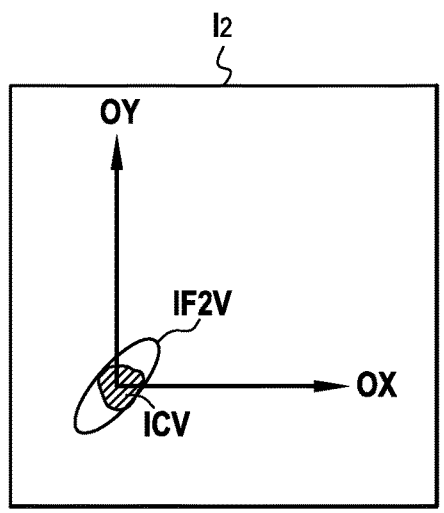
FIGS. 3E and 3F are schematic views of virtual images in each of which the image of the target and the image of the focal point are seen to coincide.
Figure 3F:
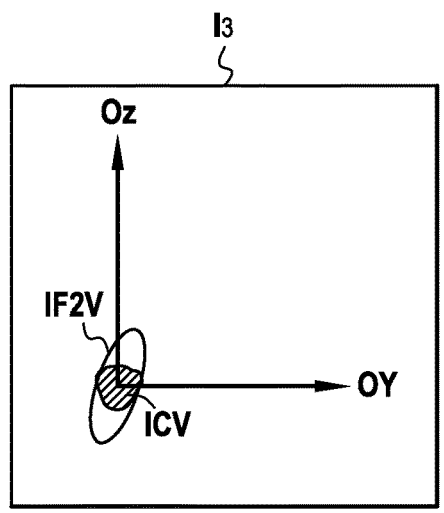

The screen 8 also allows continual visualization of the movement of the position of the virtual images IF2V and ICV subsequent to movement of the table 2. In the illustrated example, it is observed that the movement of the virtual image of the position ICV of the target draws near to the virtual image of the position IF2V of the focal point until they are superimposed (FIG. 3E, FIG. 3F). The virtual images $I_2$, $I_3$ therefore allow monitoring of the concurring or coinciding of the virtual image of the position ICV of the target with the virtual image of the position IF2V of the focal point F2.

When this coinciding position is reached, the treatment system 3 can then be guided to ensure treatment of the target C.

It is to be noted that in FIGS. 3C to 3F, the virtual image of the position IF2V of the point focal is illustrated in elliptical form corresponding to the focal volume whose spatial orientation is known by means of the second marker 24. When comparing FIGS. 3C and 3D or FIGS. 3E and 3F it is possible to ascertain the different angle of the focal volume along planes OY, OX and OZ, OY, this angle also being a function of the orientation of the generator 4.

As follows from the foregoing description, the coinciding of the focal point F2 is obtained not using the real position of the target C, but the virtual image of the position of the target C. In other words, if the virtual position of the target C corresponds to the real position of the target C, then the target C coincides with the focal point F2. However, the target C may have moved between the moment of acquisition of the position of the target C and the moment when the treatment of target C is implemented.

Therefore, when alignment is obtained, the method of the invention advantageously offers a step to confirm the coinciding between the focal point F2 and the target C.

Figure 4A:
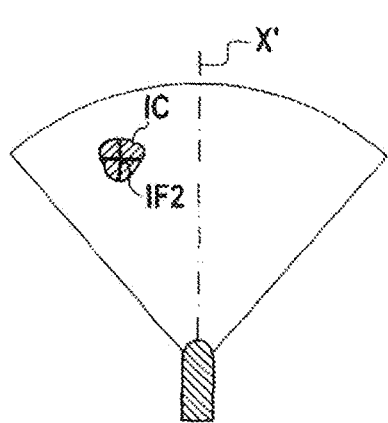
FIGS. 4A and 4B are schematic views of virtual images conforming to the invention and to the prior art respectively.

This confirmation step is performed again using the ultrasound probe 6 to locate the target C and to allow display of the image of the target IC on the screen 8 (FIG. 4A). It is to be noted that this operation to locate the target C using the ultrasound probe 6 can be freely performed or using a support 35 to hold the ultrasound probe 6 in position when the target C is located. This support 35 which is partly shown FIG. 2, allows the ultrasound probe 6 to be held in a fixed position offering the advantage of permanently visualizing the target C and any movements thereof throughout the treatment procedure, without compelling the operator to hold the ultrasound probe in position. Evidently, the ultrasound probe 6 can easily be hung on or taken off this support 35. For example, this support 35 is formed of a hinged mechanical system or flexible rod. This support 35 is not described in more detail since it is known per se and is not part of the subject matter of the invention.

Figure 4B:
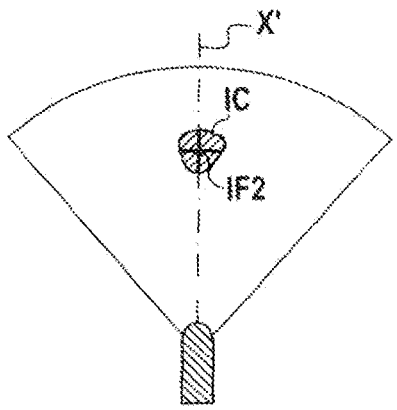

The ultrasound imaging system 5 ensures display of the ultrasound image obtained with the ultrasound probe, and hence of the image IC of the position of the target. If the coinciding of the target C with the focal point F2 has been properly carried out, then the image IC of the target C is superimposed over the image IF2 of the focal point F2. The operator is therefore again able to visualize the target C with the ultrasound probe 6 at an angle which allows the best visual quality. Unlike the prior art illustrated FIG. 4B, in which the sighting axis X' of the ultrasound probe 6 necessarily passes through the focal point F2, the sighting axis X' does not necessarily pass through the focal point F2 and this point does not necessarily lie in the centre of the image as can be clearly seen in FIG. 4A. Therefore, the image IF2 of the focal point F2 is displayed in a position independent of the sighting axis X' of the ultrasound probe 6.

When the focal point focal F2 coincides with the target C, the treatment system 3 is operated to allow the treatment phase of the target C.

If there is offset between the focal point F2 and the target C, the method comprises the renewing of the coinciding phase described above. Therefore, the method again consists of ensuring the recording of the position of the ultrasound probe 6 and of the ultrasound image $I_1$ in which the image of the target appears. This ultrasound image $I_1$ is displayed and the operator points on the position of the target C.

The position of the focal point F2 and the position of the table 2 are simultaneously recorded. The displacement values for the displacing means are calculated to allow the coinciding of the focal point F2 with the virtual position of the target C.

The display of the virtual image of the position IF2V of the focal point in relation to the virtual image of the position ICV of the target is ensured. The target C and/or the focal point F2 are moved so that, assisted by the display of the movement of the displacing means, the virtual image of the position of the target coincides with the virtual image of the position of the focal point. A new step to confirm the coinciding of the focal point F2 with the target C is then performed to verify the good match between the focal point F2 and the target C.

Figure 5A:
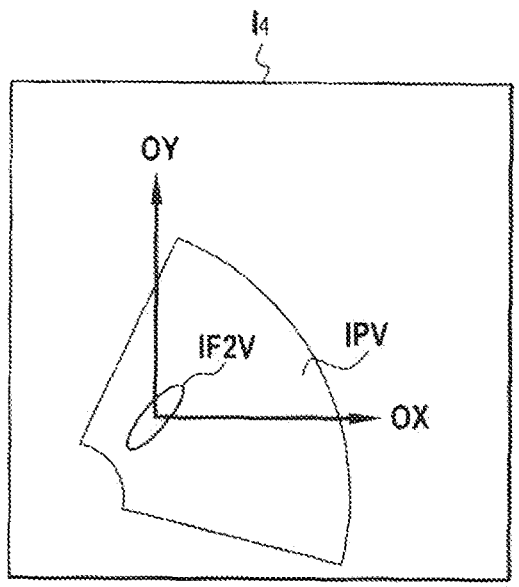
FIGS. 5A and 5B are schematic views of virtual images showing the orientation of the image plane.
Figure 5B:
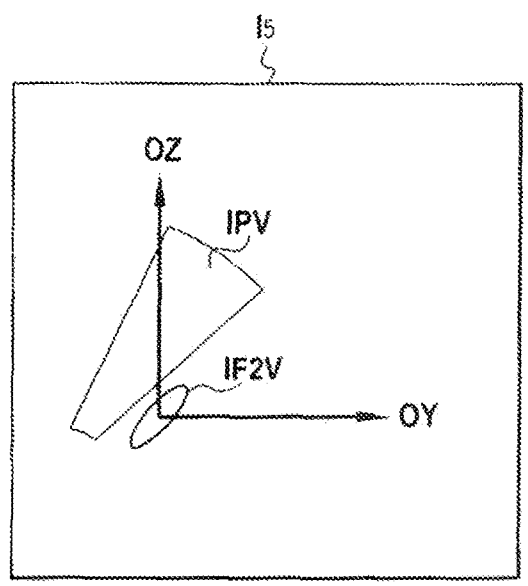

As arises from the following description, the display of the focal point F2 is transient, unlike in the prior art. For example, the focal point is displayed in the image plane when the image plane passes exactly over the focal point F2 or at certain distance therefrom e.g. +/−5 mm and preferably +/−2 mm. To help the operator to understand why the focal point disappears from the ultrasound image and which orientation must be given to the ultrasound probe 6 to retrieve the focal point, the subject matter of the invention aims at causing the image plane delivered by the ultrasound probe 6 and the focal point F2 to appear in two virtual images $I_4$,$I_5$, as illustrated FIGS. 5A and 5B. These virtual images $I_4$,$I_5$, are a projection of the three-dimensional image of the image plane delivered by the ultrasound probe 6 along planes OX,OY and OY,OZ. Therefore, the image plane of the ultrasound probe is represented by projections IPV onto the two orthogonal secant planes OXY and OYZ. The image plane of the ultrasound probe 6 and its projections IPV may contain the ultrasound image in real time such as delivered by the ultrasound imaging system 5, or a simple figurative representation of the image plane and its projections. Similarly, the focal volume is represented by projections IF2V over the two planes OXY and OYZ.

Advantageously, the information on relative altitude between the image plane and the focal volume is maintained when calculating the projections. This information is transposed to the projections, allocating semi-transparency to the image plane and full opacity to the focal volume so that, when the image plane lies in front of the focal volume, it only partly masks the latter and, when it lies behind the focal volume, the latter fully masks the image plane.

The invention is not limited to the described, illustrated examples since various modifications can be made thereto without departing from the scope of the invention.

What is claimed is:

1. A method for locating and visualizing a target belonging to a mammal, in relation to a focal point of a treatment system using acoustic pressure waves, the method comprising:

providing a table supporting the mammal caring the target, providing an ultrasound imaging system comprising an ultrasound probe delivering an ultrasound image of an image plane, at least one of the target and the treatment system being moved by displacing means, to cause the target to coincide with the focal point, linking said ultrasound probe solely via an electric connection cable to a computing and control unit comprising a screen, said ultrasound probe comprising a grasping handle and being mobile in space, mechanically independent of the treatment system, and located by a remote locating system when it lies within a detection volume of the remote locating system, moving the ultrasound probe with hands within the detection volume to visualize an image of the target in the ultrasound image of the image plane displayed on the screen, calculating positions of the ultrasound probe, the focal point, and the table, during a treatment of the mammal, using the locating system, selecting and recording the ultrasound image in which the image of the target appears, simultaneously recording the position of the ultrasound probe located by the remote locating system, and freezing, on the screen, the selected and recorded ultrasound image in which the image of the target appears, selecting a position of the image of the target by pointing on the recorded frozen ultrasound image, calculating, using the computing and control unit, a virtual position of the target from the position of the target from the pointing of the position of the image of the target, and from the position of the ultrasound probe simultaneously recorded with the recording of the ultrasound image in which the image of the target appears, simultaneously determining, firstly, a position of the focal point of the treatment system by means of the remote locating system, and, secondly, a position, by means of the remote locating system, of the displacing means moving at least one of the target and the treatment system, calculated displacement values for the displacing means which are sufficient to allow the virtual position of the target to coincide with the focal point based upon the virtual position of the target, and the positions of the focal point and of the displacing means, moving at least one of the target and the focal point via the displacing means in accordance with the calculated displacement values, so as to cause the virtual position of the target to coincide with the image of the focal point, the method further including steps to confirm the coinciding of the focal point with the target, the steps comprising displaying the image of the focal point to verify that the focal point and target coincide, wherein displaying of the image of the focal point is performed such that the image of the focal point is transiently displayed in the ultrasound image of the image plane delivered by the ultrasound probe only when the image plane passes exactly over the focal point, or within a predetermined distance from the focal point.

2. The method according to claim 1, comprising determining the position of the displacing means by means of the remote locating system.

3. The method according to claim 1, comprising ensuring the display of the displacement values calculated for the displacing means, and updating these displacement values in relation to the movement made.

4. The method according to claim 1, comprising ensuring the display of two virtual images, each virtual image being a projection of the ultrasound image on one of the two orthogonal secant planes, and causing to appear, in each of the two virtual images, the image of the virtual position of the target and the image of the virtual position of the focal point, and their respective movements subsequent to movement of the displacing means.

5. The method according to claim 1, comprising, by means of the remote locating system, accessing to a spatial orientation of a marker attached to a body of a generator of the treatment system, and visualizing, by the screen, an orientation of a focal volume of the treatment system.

6. The method according to claim 1, comprising displaying the image of the focal point in a position independent of the sighting axis of the ultrasound probe.

7. The method according to claim 1, comprising displaying, in the ultrasound image, the image of the focal point when the plane of the ultrasound image lies secant to the focal point.

8. The method according to claim 1, wherein the mammal is a human being.

9. The method according to claim 1, further comprising:
creating, on the screen, at least two virtual images, each image being a projection of one of two orthogonal secant planes, and causing to appear in each thereof, the image of the virtual position of the target and the image of the focal point, and
visualizing, on the virtual images, from calculated displacement values, the movement of the image of the virtual position of the target and the movement of the image of the focal point when causing the virtual image of the target to coincide with the focal point by the displaying means.

10. The method according to claim 1, further comprising causing the image plane delivered by the ultrasound probe, and the focal point, to appear in two virtual images which are each a projection of an image of the image plane delivered by the ultrasound probe onto two orthogonal secant planes.

11. The method according to claim 1, wherein the image of the focal point is displayed in the image plane only when the image plane is at a distance of +/−5 mm from the focal point.

12. The method according to claim 1, wherein the image of the focal point is displayed in the image plane only when the image plane is at a distance of +/−2 mm from the focal point.

13. The method according to claim 1, including steps to confirm the coinciding of the focal point with the target, the steps comprising:
moving the ultrasound probe to locate the target, allowing the display of the image of the target on the screen, and
ensuring the recording of the position of the focal point and the display of the image of the focal point, to verify that the focal point and target coincide, for operating the treatment system.

14. The method according to claim 13, wherein the confirmation steps, in the event of offset between the focal point and the target comprise:
moving the ultrasound probe to visualize the target in an image displayed on the screen,
simultaneously recording, firstly, the image in which the image of the target appears, and, secondly, the position of the ultrasound probe,
selecting the position of the image of the target in the recorded image,
simultaneously determining, firstly, the position of the focal point and, secondly, the position of the displacing means, and calculating the displacement values for the displacing means to cause the focal point to coincide with the virtual position of the target, and of moving at least one of the target and the focal point via the displacing means so as to cause the virtual position of the target to coincide with the focal point.

* * * * *